(12) United States Patent
Rezzonico et al.

(10) Patent No.: US 7,529,575 B2
(45) Date of Patent: May 5, 2009

(54) NUCLEAR MAGNETIC RESONANCE IMAGING DEVICE

(75) Inventors: Fabio Rezzonico, Como (IT); Orfeo Contrada, Genoa (IT); Gianni Sarasso, Genoa (IT)

(73) Assignee: Esaote S.p.A., Casale Monferrato (IT)

( * ) Notice: Subject to any disclaimer, the term of this patent is extended or adjusted under 35 U.S.C. 154(b) by 598 days.

(21) Appl. No.: 10/928,106

(22) Filed: Aug. 30, 2004

(65) Prior Publication Data

US 2005/0049491 A1 Mar. 3, 2005

Related U.S. Application Data

(60) Continuation-in-part of application No. 10/043,151, filed on Jan. 14, 2002, now Pat. No. 6,801,038, which is a division of application No. 09/412,636, filed on Oct. 5, 1999, now Pat. No. 6,346,814.

(30) Foreign Application Priority Data

Oct. 5, 1998 (IT) .............................. SV98A0052

(51) Int. Cl.
*A61B 5/055* (2006.01)
(52) U.S. Cl. .................. 600/410; 324/318; 324/322
(58) Field of Classification Search ................. 600/408, 600/436, 407, 410; 324/309, 318, 322
See application file for complete search history.

(56) References Cited

U.S. PATENT DOCUMENTS

| 2,846,543 | A | | 7/1958 | Hansen et al. | |
|---|---|---|---|---|---|
| 3,466,439 | A | | 9/1969 | Setälä | |
| 3,967,129 | A | * | 6/1976 | Winkler | .................... 250/517.1 |
| 4,062,518 | A | | 12/1977 | Stivender et al. | |
| 4,581,538 | A | * | 4/1986 | Lenhart | .................... 250/519.1 |
| 4,725,781 | A | | 2/1988 | Röschmann | |
| 5,329,924 | A | | 7/1994 | Bonutti | |
| 5,541,515 | A | | 7/1996 | Tsujita | |
| 5,644,231 | A | | 7/1997 | Wignall | |
| 5,735,278 | A | * | 4/1998 | Hoult et al. | .................. 600/422 |
| 5,986,531 | A | * | 11/1999 | Carrozzi | ...................... 335/301 |
| 6,313,632 | B1 | | 11/2001 | Aoki et al. | |
| 6,346,814 | B1 | | 2/2002 | Carrozzi et al. | |
| 2002/0057088 | A1 | * | 5/2002 | Carrozzi et al. | .............. 324/318 |

* cited by examiner

*Primary Examiner*—Ruth S Smith
*Assistant Examiner*—Peter Luong
(74) *Attorney, Agent, or Firm*—Buchanan Ingersoll & Rooney PC

(57) ABSTRACT

A nuclear magnetic resonance imaging device has a magnetic structure which defines a cavity for housing at least part of the body of a patient with a magnetic field which permeates at least part of the cavity, an opening provides access to the imaging cavity from outside of the magnetic structure and electrically conductive and electrically grounded shielding provided at the opening is movable between a first inactive configuration wherein the opening is substantially open and an active configuration in which the opening is at least partially closed by the shielding.

37 Claims, 12 Drawing Sheets

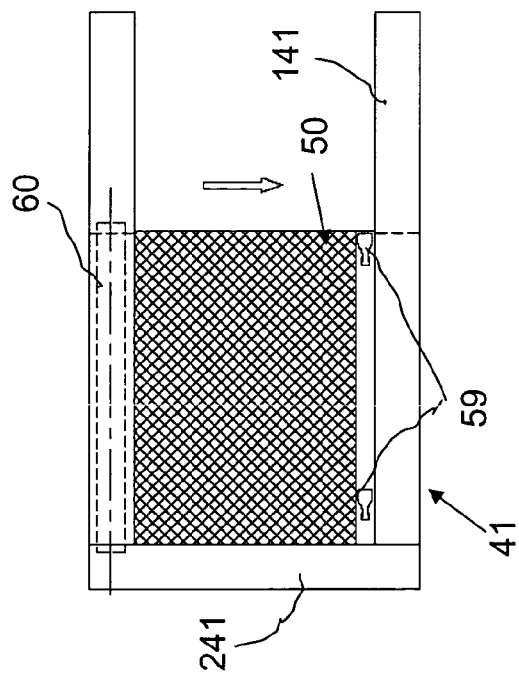
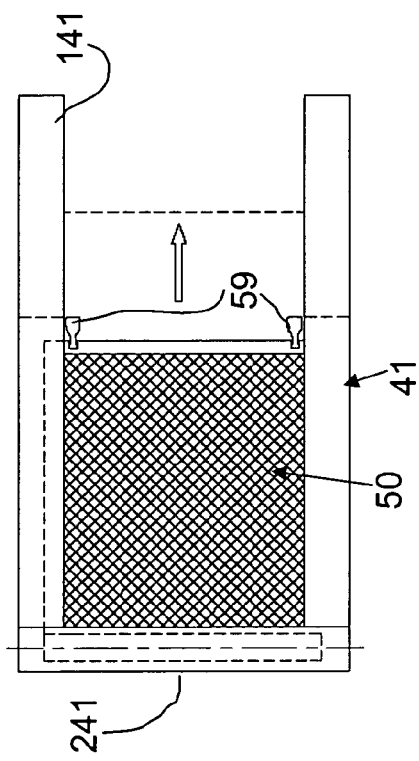
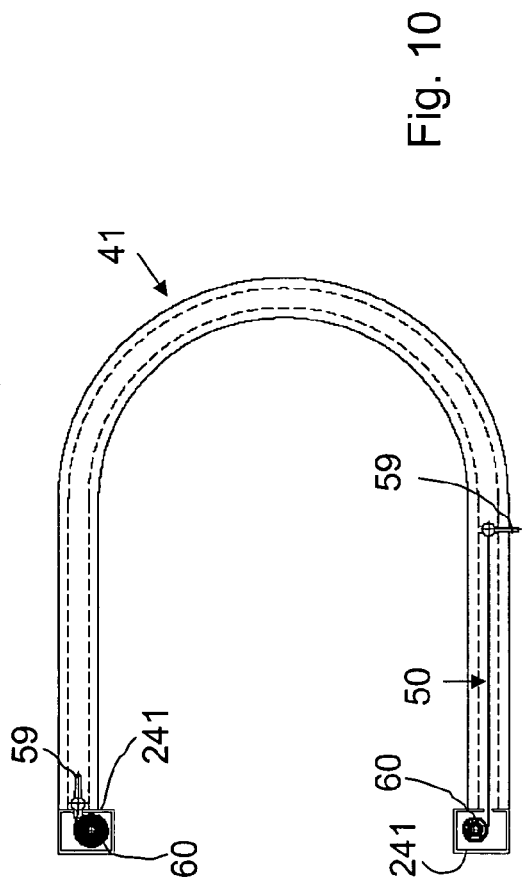
Fig. 11
Fig. 10
Fig. 9

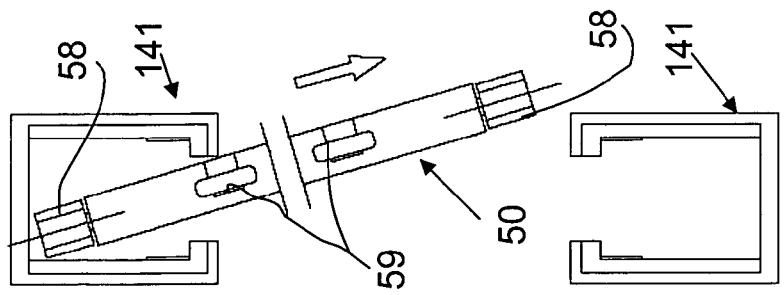
Fig. 12E
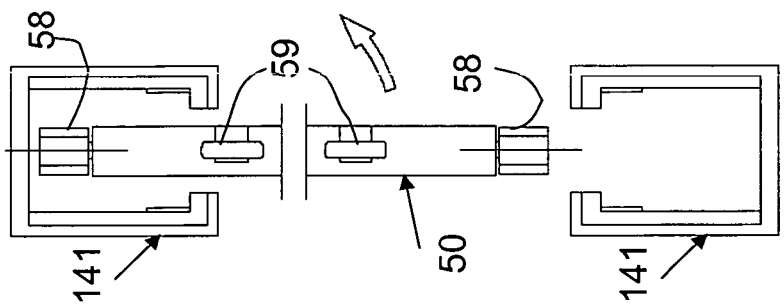
Fig. 12D
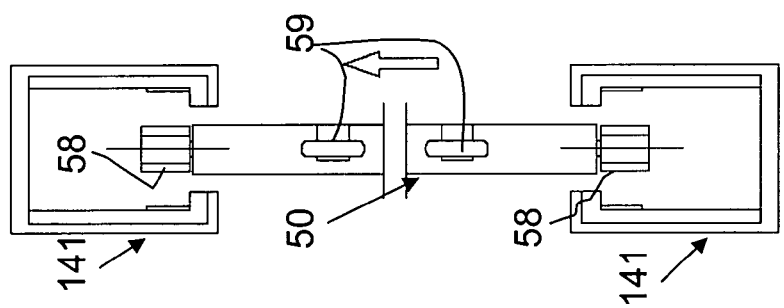
Fig. 12C
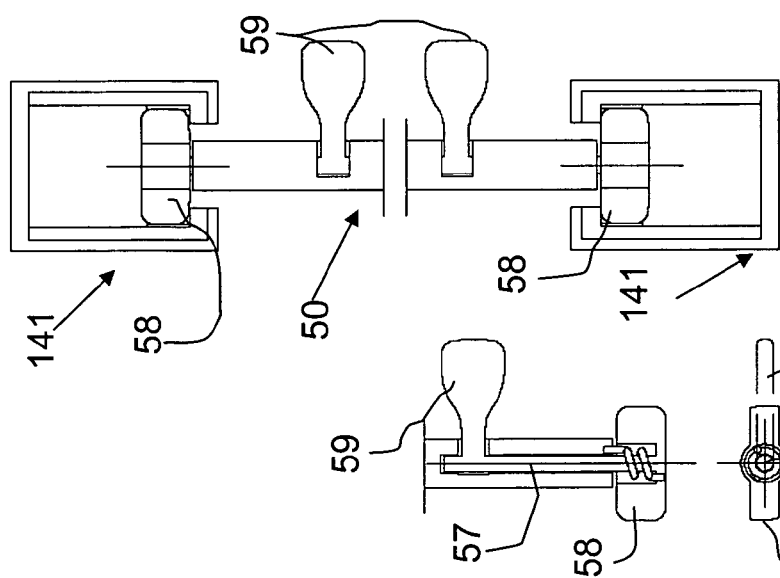
Fig. 12B
Fig. 12A

NUCLEAR MAGNETIC RESONANCE IMAGING DEVICE

This application is a continuation-in-part of application Ser. No. 10/043,151 filed on Jan. 14, 2002, now U.S. Pat. No. 6,801,038, and which is a divisional of application Ser. No. 09/412,636 filed on Oct. 5, 1999, now U.S. Pat. No. 6,346,814.

FIELD OF THE INVENTION

The invention relates to a Nuclear Magnetic Resonance Imaging device having at least one rigid shielding member for at least partially closing one or more open sides, which can be moved between a first open position and a second (at least partially closed) position, the at least one rigid shielding member preferably being made of an electrically conducting material or coated with layers made of an electrically conducting material.

BACKGROUND OF THE INVENTION

An object of the present invention is to provide improvements in the electromagnetic shielding of MRI scanners by at least closing parts of the openings of the scanners which do not need to be open to allow the body under examination to access a cavity of the device where the imaging occurs.

SUMMARY OF THE INVENTION

Particularly in MRI devices which are of the so called dedicated type, where the MRI scanner is relatively small so that the entire body of the patient cannot be housed inside the imaging cavity and also where the static magnetic field generated within the imaging cavity is of low or medium field strength, it is desirable to reduce the infiltration of electromagnetic noise inside the cavity and in the receiving coil. MRI signals are relatively low in strength and electromagnetic noise can reduce the quality of the acquired image. One solution known in the art to address this situation consists of at least reducing the opening of the imaging cavity by using electromagnetic shields which are grounded together with the electromagnetic shields provided in the scanner itself. Other kinds of shields have also been used. One optimum solution provides grounding the body of the patient under examination through the shields.

Devices having only one or two opposite openings for accessing the imaging cavity of the scanner can have simple solutions. However, problems arise when the scanner is not annular in shape. Scanners which have a "C-shape" or a "U-shape" have three open sides and it is particularly difficult to shield the imaging cavity of these devices. These kinds of MRI scanners allow different body parts of the patient to be positioned in the scanner. For positioning the different body parts in the scanner, different portions of the three open sides of the scanner are occupied by the patient so that a very flexible and also rapidly movable shielding member is needed.

The present invention provides for an MRI apparatus which has in combination a shielding member which can rapidly assume different configurations to partly close the open sides of the imaging cavity and with relatively simple devices. Furthermore, it is an object of the present invention to provide an MRI device having a shielding member which can maintain a temporary configuration for imaging a certain body part or anatomical region thereby reducing the time consuming process of closing the opening with an electromagnetic shield.

BRIEF DESCRIPTION OF THE DRAWING FIGURES

The present invention will appear more clearly from the following detailed description of several embodiments illustrated in the enclosed figures in which:

FIGS. 9 and 10 are respectively a side view and a sectional view according to a section plane parallel to the guides of the embodiment according to FIGS. 8A and 8B in which the shielding curtain is formed by a net;

FIG. 11 is a variation of the embodiment according to FIGS. 8A to 10 in which a roller blind type shielding panel or curtain has a roller housed in a straight part of the upper guide;

FIGS. 12A and 12B illustrate a particular embodiment (with cross section) of a locking mechanism of the shielding curtain according to FIGS. 8A to 11;

FIGS. 12C, 12D and 12E illustrate the embodiment of FIGS. 12A and 12B applied to a shielding panel of FIGS. 1 to 7B and in which the panel is disengageable and engageable in the upper and lower guides using the locking mechanism according to FIGS. 12A and 12B;

DETAILED DESCRIPTION OF THE INVENTION

Figure 1:
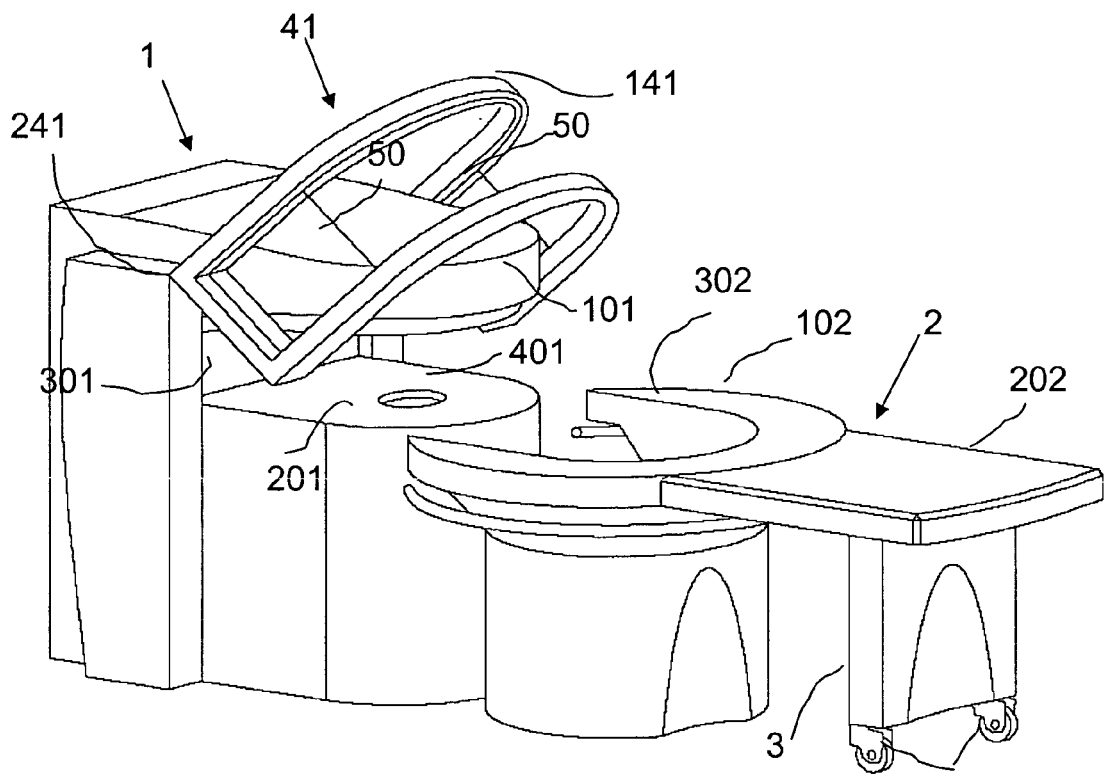
FIG. 1 is a perspective view of an MRI apparatus having a shielding member according to a first embodiment of the present invention.
Figure 2:
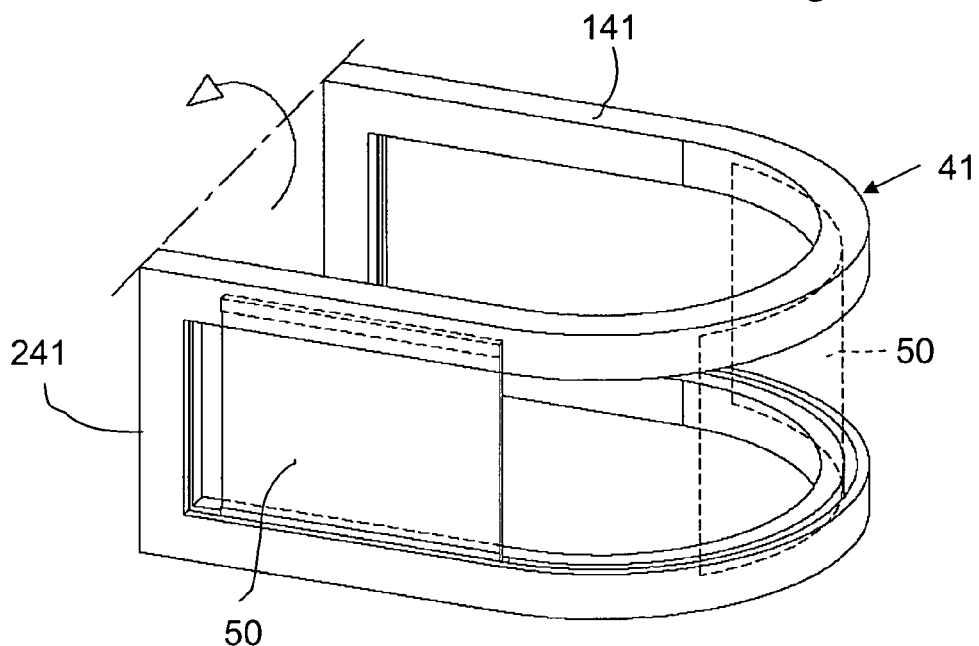
FIG. 2 is an enlarged view of the shielding member of FIG. 1.

Referring to FIGS. 1 to 3, a Nuclear Magnetic Resonance Imaging device comprises a magnetic structure 1. The magnetic structure 1 shown in these figures is C-shaped and defines an imaging cavity with three open sides about its perimeter. The cavity is defined by an upper side 101, a lower side 201 and a vertical side 301. These three sides 101, 201, and 301 cover the magnetic structure and other operating members, and are made of an appropriate material, e.g. of plastic or the like, and the imaging cavity has a recess 401, in a predetermined area, for accommodating a fastening base of a receiving coil (not illustrated). The magnetic structure enclosed by the cover is formed by two spaced apart plates of ferromagnetic material and forms a yoke which is connected together by a vertical wall. Two poles covering an intermediate layer of magnetized material are supported to the inner sides of the horizontal plates.

The free end edges of the upper and lower sides 101 and 201 are rounded, preferably with a semicircular profile.

A table 2 is associated with the magnetic structure 1. The table 2 consists of a first part 102 and a second part 202. The first part 102 has a supporting surface with a hollow region 302 which has a shape that is complementary and a size corresponding to the lower side 201 of the magnet 1. Although the first part 102 can have any outer shape, it preferably has a circular segment shape with an angular extension of more than 180°, so as to fully surround the central U-shaped hollow, preferably with a circular rounded portion. The first part 102 of the table is designed to be fitted around the side 201 of the magnet 1, which complements the supporting surface. The first part 102 of the table is supported by at least a pair of wheeled legs (not shown), which are provided at least in the end side of the first part that is configured to connect to the second part 202 of the table which is also supported by one of more legs 3 having wheels 4. The one or more legs 3 are provided on the end side of the second part 202 of the table opposite to the end which connects to the first part 102.

The magnetic structure 1 may be provided with a member 41 for shielding electromagnetic noise, which is configured in the form of a rigid oscillating frame or shield frame 141 which carries shielding panels or shielding curtains that are slidable about the frame.

In the illustrated embodiments, the shield frame 141 and the shielding panels or curtains can have any desired amount of extension in order to close partially or completely one, two or all three open sides of the magnetic structure. Obviously, shielding panels or curtains with different amounts of extension may be also provided either alternatively or in combination.

As shown in the figures, the shield frame 141 is U-shaped and has a shape which is complementary to the outside perimeter of the upper and lower sides of the magnetic structure 1. The shield frame 141 is hinged so as to be able to oscillate about a horizontal axis, parallel to the closed vertical side 301. In the preferred embodiment, the axis is substantially at the same level as or at a slightly higher level than the upper side 101 of the magnetic structure 1.

The shield frame 141 is formed by two "U-shaped" guides which are held at a distance corresponding substantially to the distance between the two horizontal upper and lower sides 101, 201 of the magnetic structure 1 by transverse elements 241 that connect the two "U-shaped" guides at their corresponding ends. The distance of the "U-shaped" guides is such that by oscillating the frame downward into the area of the open sides, the frame substantially encompasses the edges of the upper and lower sides of the magnetic structure defining the cavity and abuts to the peripheral surfaces of two plates which form the upper and lower sides. In the preferred embodiment, the shield frame 141 is made of or provided with an electrically conducting material or is coated by a layer made of an electrically conducting material.

In the present embodiment, electrical connections which interact with complementary electrical connections disposed in a corresponding position on a contact surface of the first part 102 of the table and/or on the side 201 of the magnet are provided at the peripheral edges and possibly also at the faces of the "U-shaped" frame 141 which overlay the peripheral edges of the upper plates of the magnetic structure 1 at which the frame is hinged. Along the "U-shaped" guides, at least one shielding plate or one shielding curtain may be provided. The shielding plate and the shielding curtain each engages with their edges the upper and the lower guides of the "U" shaped frame 141. Furthermore the shielding plate and the shielding curtain are preferably made of or layered with electrically conductive material which ends with electric contact elements at the edges engaged in the guides. These elements cooperate with electrical contact elements provided in the two guides. The contact elements are configured to allow sliding and thereby also provide an electrically conductive contact between the shielding panel or the shielding curtain and the guides.

FIG. 2 illustrates a shielding panel 50 in the form of a rigid but flexible thin plate. The shielding panel can slide along the guides in which it is engaged with its upper and lower edges. In FIG. 2, the shielding panel 50 is shown with continuous lines in a first position and with discontinuous lines in a centered position at the rounded central part of the "U-shaped" guides.

Figure 3A:
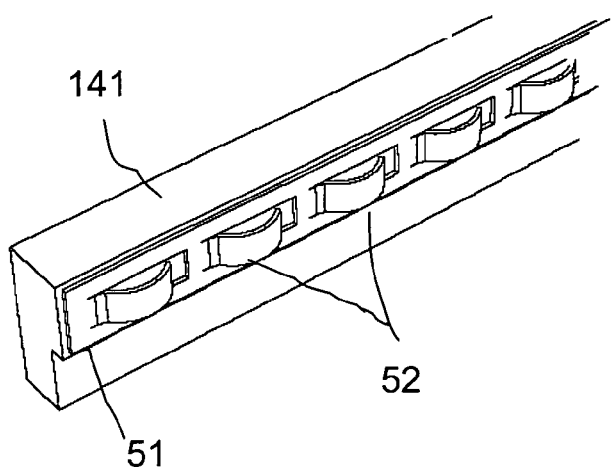
FIGS. 3A and 3B illustrate a particular embodiment of electrical contact elements of guides of a shielding frame with shielding panels or curtains.
Figure 3B:
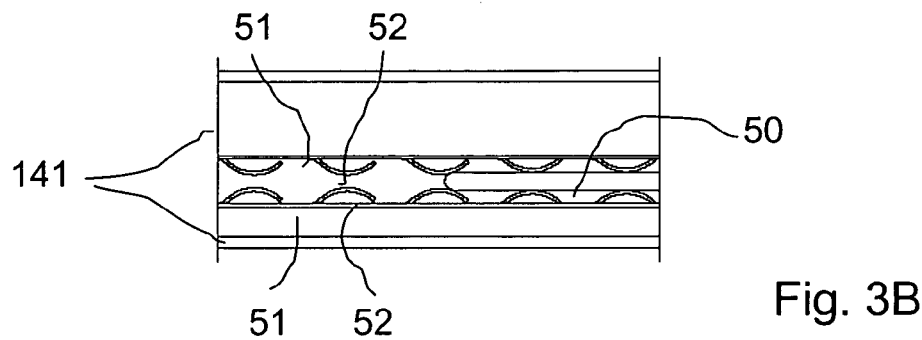

FIGS. 3A and 3B illustrate an embodiment of the electrically conductive contacts which can be provided inside the guides. In this embodiment, a row of tongues 52 are cut out from a track 51 of electrically conductive material. The tongues 52 are connected at one longitudinal end to the track 50 and they further have a convex shape with which they protrude from the track surface toward the center of the guide. Such contact elements can be provided on both side walls of the guides and the panel 50 can slide between each pair of facing tongues 52 which come into electrical contact with a continuously electrically conductive track on each side of the panel, as illustrated in FIG. 3B.

Figures 4A, 4B, 4C:
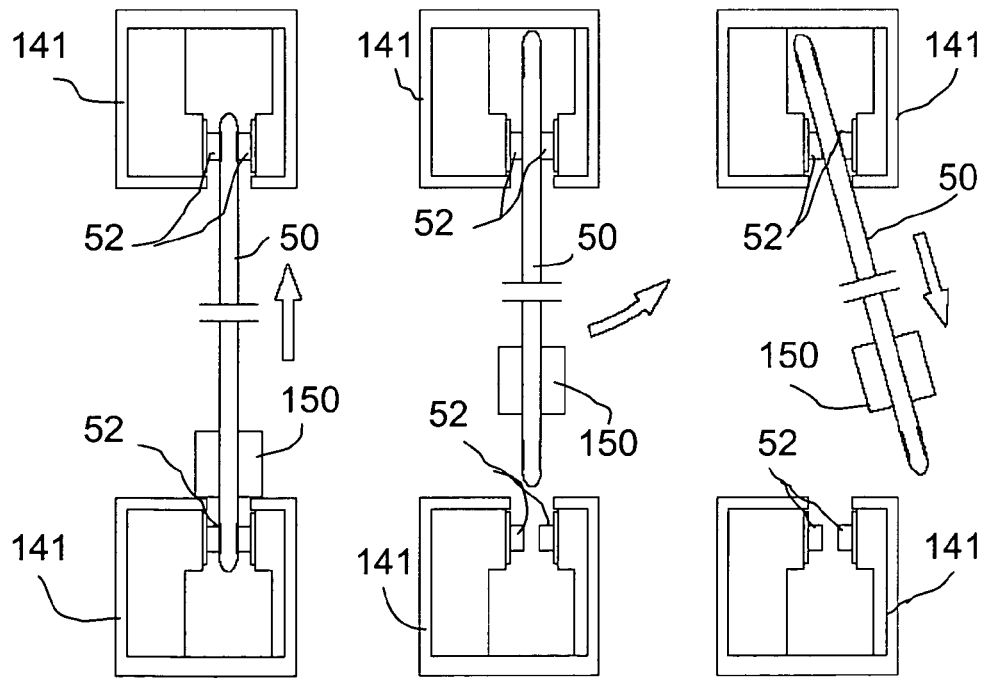
FIGS. 4A to 4C illustrate three sectional views of the shielding member according to the invention in which the shielding panel can be engaged and disengaged from the guides in different stages of the disengaging proceeding.

With reference now to FIGS. 4A to 4C, a cross sectional view shows the panel engaged in the two opposite guides provided with the electrically conductive tongues. According to a further improvement, as illustrated in FIGS. 4A to 4C, the shielding panel 50 may be engageable and disengageable with the guides. This can be achieved in several ways. One of the several ways is illustrated in FIGS. 4A to 4C. Due to the fact that the panel is substantially vertical, at least while in the active position of the shield, i.e. when the shield is swung downwards, the dimension of the panel perpendicular to the guides is less than the distance of the bottom wall of the guides, but sufficient to be brought into an engaged position in which the two opposite edges of the shielding panel still remain engaged between the rows of electrically conductive contact elements 52 on the lateral sides of the guides. Advantageously, these contact elements, in this example the tongues 52, are positioned near the side of the guide opposite to their bottom. At a certain distance of the lower edge of the panel, limiting lateral protrusions 150 are provided which limit the depth of penetration of the lower edge of the shielding panel 50 in the lower guide at a level at which the upper edge of the shielding panel still is engaged between the two facing rows of electrically conductive contact elements, i.e. the tongues 52. These protrusions 150 abut against an upper side of the lower guide along which the limiting protrusions slide when the shielding panel is displaced.

Thus for disengaging the shielding panel from the guides, the panel can be shifted upwardly until the lower edge can slip out of the lower guide, then the panel can be inclined laterally, bringing the lower edge away from the lower guide, so that by sliding the panel downward also the upper edge can be disengaged from the upper guide. In order to engage a shielding panel into the guides, one can carry out movements which are the reverse of the ones described above for disengaging the shielding panel from the guides.

This further improvement allows one to provide a series of differently dimensioned shielding panels (referring to their dimension in the direction of sliding along the guides). The differently dimensioned panels can be used alternatively to one another or in combination, it being possible to engage two or more panels in the guides to form a shielding wall inside the "U-shaped" frame which closes as much as possible of the open sides of the magnetic structure, leaving open only passages having dimensions that are limited to the strictly necessary dimensions for introducing a body or an anatomical part of a body inside the cavity of the magnetic structure.

Thus the opening of the shielding member can be varied according to the dimensions of the patient and to the morphology of the anatomical part which has to be placed into the imaging cavity of the magnetic structure. Furthermore due to the fact that the entire frame 41 of the shielding member can be swung upwardly, the imaging cavity can be completely opened without the need to change the position of the shielding panel, so that it is possible to access the cavity of the magnetic structure for carrying out operations without changing the position of the shielding panel or shielding panels.

The electrical contact of the frame of the shield member to ground (i.e., to earth potential) can be obtained through the hinges which can be made of electrically conductive material. In addition, the electrical contact of the frame to ground can be obtained by further electrically conductive contact elements which are positioned on the contact surfaces of the frame 141 which abut against contact surfaces at the periphery of the upper plate of the magnetic structure, at the patient table or at the lower plate of the magnetic structure and at the transverse wall connecting the upper and lower plates. The contact surfaces can be provided as illustrated in FIG. 15A with analogous contact elements as the one described for the guide and illustrated in FIG. 3.

Figure 15A:
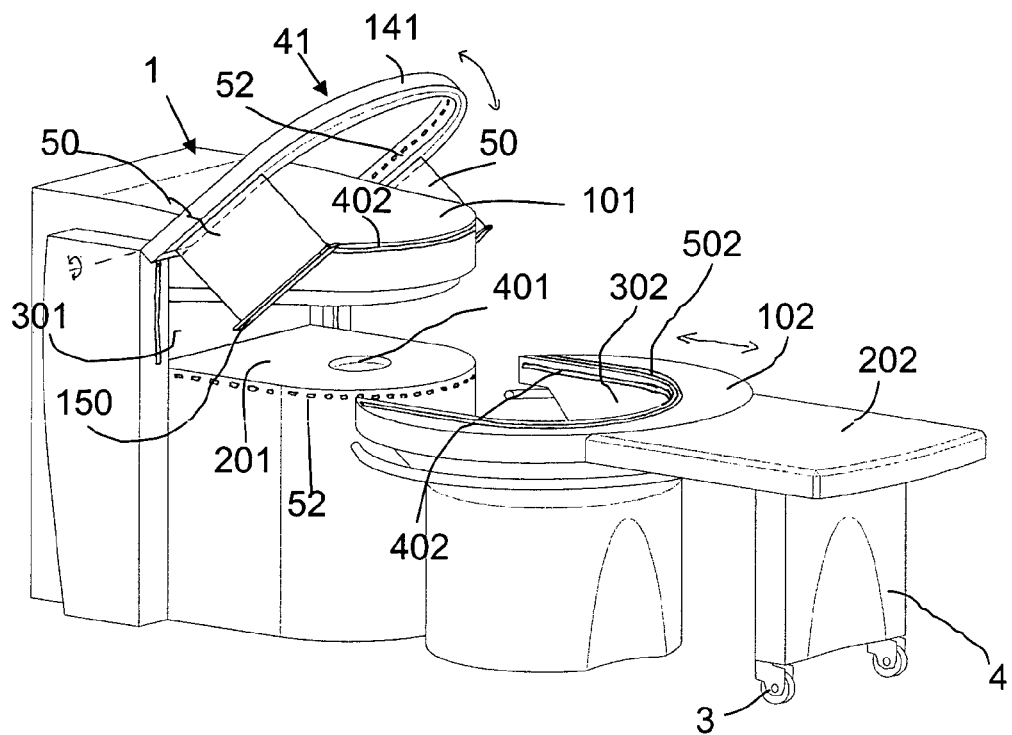
FIGS. 15A and 15B illustrate a variation of the arrangement of FIG. 1 according to the present invention in which a frame of the shielding member has only one upper guide and no lower guide and the shielding panels or curtains hang free from the upper guide, while in FIG. 15A the table is not coupled to the magnetic structure and in FIG. 15B the table is coupled to the magnetic structure.

Alternatively, the contact elements on the contact surface of the frame of the shielding member or the contact surfaces at the periphery of the upper plate of the magnetic structure, at the patient table or at the lower plate of the magnetic structure and at the transverse wall connecting the upper and lower plates, may be formed by an electrically conductive track which is continuous while the other contact surface carries the contact elements according to FIG. 15A.

By providing several shielding panels which can be engaged together in the frame of the shielding member, each shielding panel can be provided with electrically conductive elements at edges oriented transversally with respect to the sliding direction, so that an electrical contact can also be established between adjacent shielding panels. The contact elements can be a peripheral edge or band of electrically conductive material or contact elements can be provided which are made according to the example of FIGS. 6A to 6C.

Figure 5A:
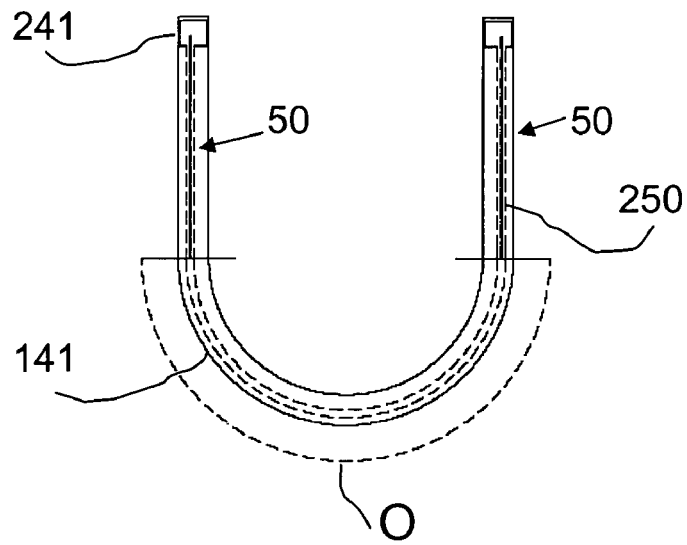
FIGS. 5A to 5c illustrate a simplified top view of the frame of the shielding member in combination with a variant of the shielding panel, while in each figure different positions of the shielding panel in the frame are illustrated.
Figure 5B:
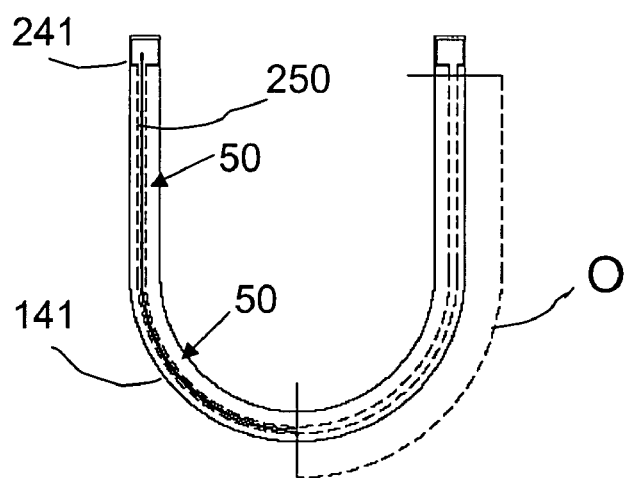
Figure 5C:
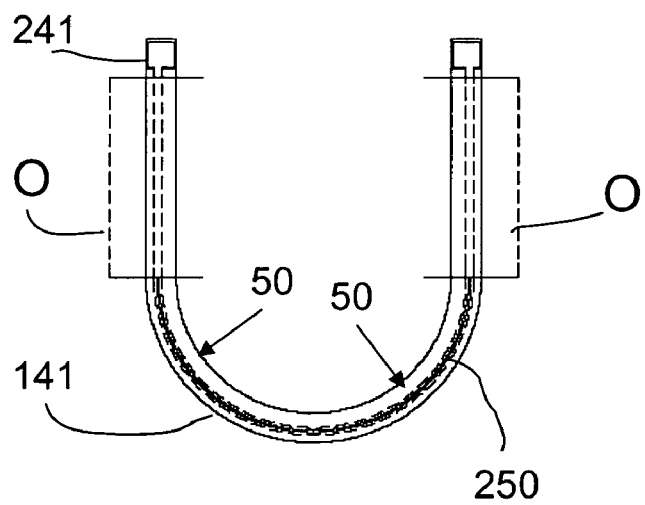

FIGS. 5A to 5C illustrate a variation of the shielding panel. In this case, the shielding panel is formed by several staves 250 which are hinged one to the other. In this embodiment, for example, the staves may be hinged by an external coating layer of plastic material which forms a hinge film between each two adjacent staves. The staves and/or at least one of the layers can be made or layered with electrically conductive material. Alternatively, or in combination, a further layer of electrically conductive material can be provided as an intermediate layer between the staves and one or both of the external coating layers. Also, in this example, the shielding panel is provided with electrically conductive contact elements or with an electrically conductive track at one, and preferably at both, edges engaged in the guides of the frame of the shielding member.

The electrical contact elements of the guides can be made according to the previously described example of FIG. 3. The staved shielding panel according to FIGS. 5A to 5C can also be engageable and disengageable in and from the frame of the shielding member in a similar way as described in connection with the embodiment of FIGS. 4A to 4C.

FIGS. 5A to 5C illustrate different positioning of the shielding panel in the frame of the shielding member. In the present example, two staved panels are provided which can be engaged together in the frame of the shielding member in order to obtain different configurations of partially closing the open sides of the magnetic structure. In FIG. 5A, a frontal opening is left free substantially corresponding to the arched part of the frame of the shielding member. The width of the opening is illustrated with dotted lines and the lateral limits are illustrated with a continuous line. The open part of the shielding member is indicated by "O". Considering the above described embodiments, it appears clearly that the open sides of the shielding member are not completely closed by the body under examination which has normally rounded shapes. In this case, as it will be described later on, the remaining open spaces between the body part passing through the openings left free in the shielding member and the shielding frame can be completely closed by providing soft cushion-like elements having an outer layer of electrically conductive material and which can provide for an electrical contact between the frame, the edges of the shielding panel and the part of the body passing through the opening. To this end, the frame of the shielding member can have further electrically conductive contact elements which are positioned on the surfaces oriented against the internal part of the frame. The electrically conductive track on the lower guide will provide for a direct contact with the part of the body which lays on it, although depending on the morphology an electrically conductive insert in the form of a cushion can be provided also between the lower guide and the body part or from the upper side of the guides. The electrically conductive inserts are pressed between the part of the body passing through the openings left free in the shielding member and the corresponding parts of the frame of the shielding member and the edge or edges of the shielding panels.

Figure 6A:
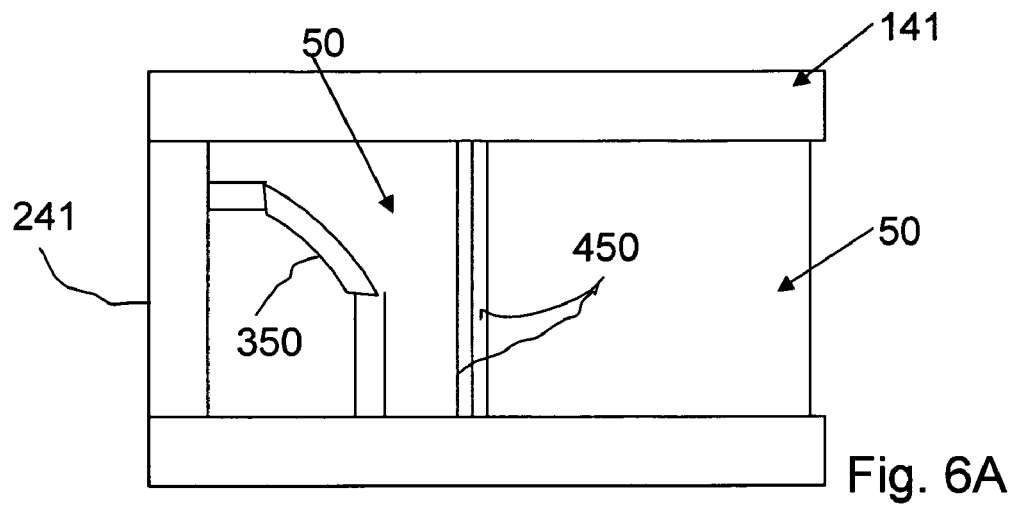
FIGS. 6A to 6C illustrate a side view of the shielding member according to the previous embodiments in which an end panel having a shaped contact edge or a shaped opening with a shaped contact edge is provided, which shapes corresponds to the shapes of the parts which have to access the cavity of the magnetic structure by passing through the shielding member.
Figure 6B:
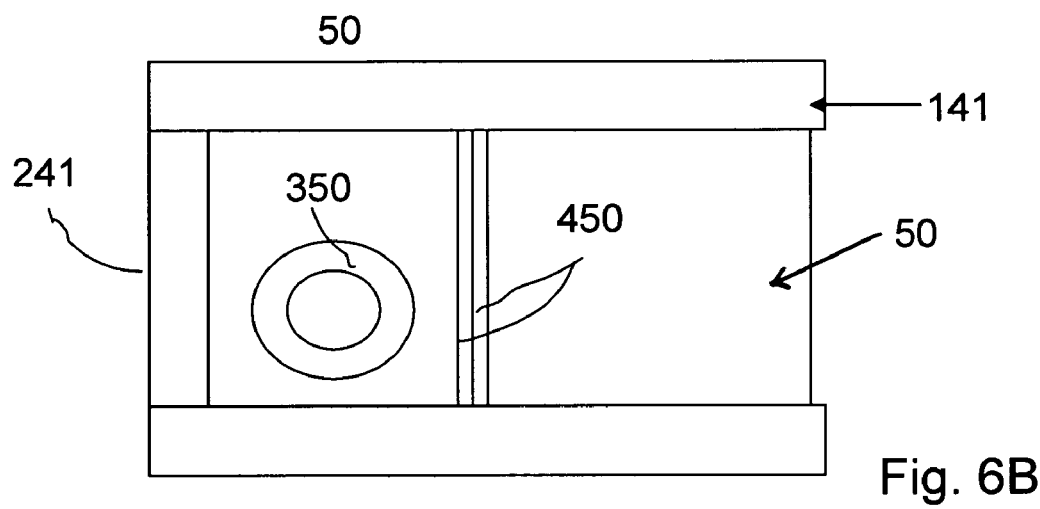
Figure 6C:
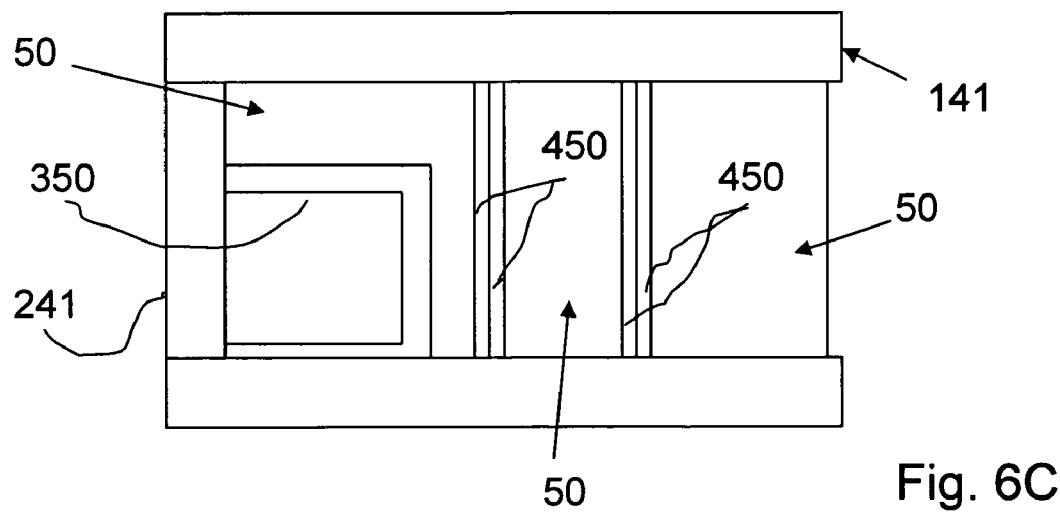

Alternatively or in combination, the shielding panels can be provided with at least one edge which is transverse to the sliding direction and which is shaped according to the morphology of the body part which has to pass through the opened side. An example is shown in FIGS. 6A and 6C. In this case, a shaped edge 350 may be made by a soft compressible element which has an external electrically conductive layer which is in electrical contact with the electrically conductive material of the shielding panel. Thus the shaped edge of the shielding panel can be easily adapted to the different morphologies of the same body part due to dimensional differences among different patients. The shaped edge can also exert a certain action of compression against the part of the body passing through the opening in the shielding member in order to provide for a better electrical contact between the human body and the shielding member. The shaped edge of the shielding panel can be made in the form of a shielding pillow as described above or it can be made by a tubular element which is secured to the edge of the shielding panel and which is made of elastic material such as rubber or the like. The tube may be made of electrically conductive rubber or have an external layer of electrically conductive material such as electrically conductive tissue.

Due to the fact that the shielding panels can be engaged and disengaged in and from the frame of the shielding member, several shielding panels having differently shaped edges for fitting and electrically contacting the part of the body passing through the opening in the shielding member can be provided. These shielding panels can have a short extension in the direction of sliding so that they can be used as end shielding panels in combination with further shielding panels forming the major or central part of the shielding member.

Furthermore, different panels 50 having different dimensions in the direction of sliding can be provided as illustrated in FIG. 6C. The shielding panels having the shaped edge 350 and the other shielding panels having different dimensions in the direction of sliding can have contact edges 450 which are of electrically conductive material, and which while abutting against the facing edge of an adjacent panel, provide for the continuity in the electrical conduction between adjacent panels of the shield.

As illustrated in FIG. 6C, alternatively a shielding panel or curtain can be provided with an opening which is defined by an electrically conductive edge 350 similar to the shaped edge.

Figure 7A:
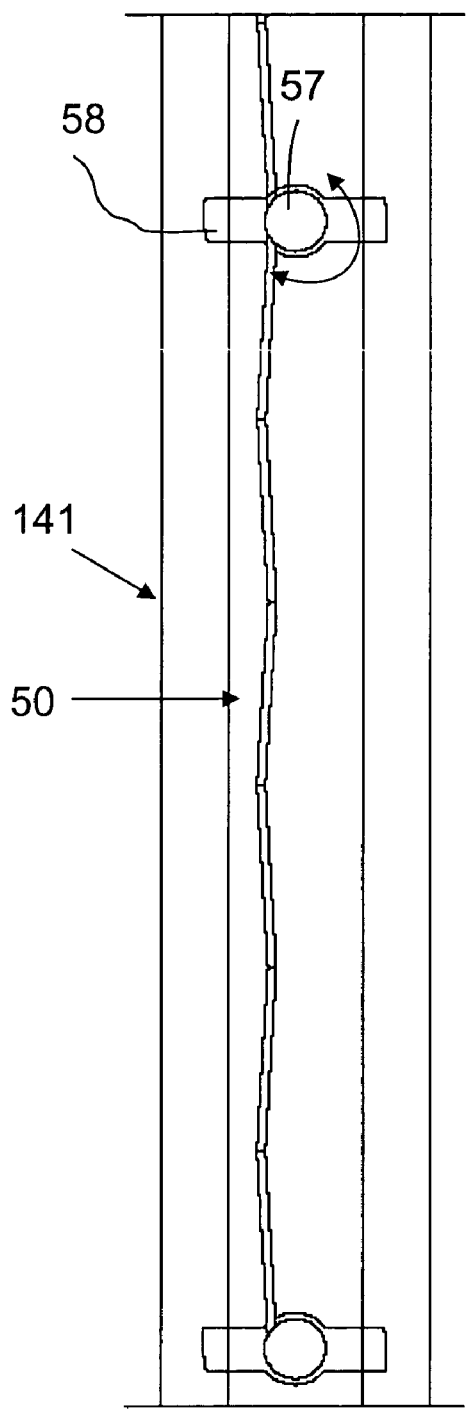
FIGS. 7A and 7B illustrate another embodiment of a shielding panel which is of the bellows or folding door type in an elongated and in a retracted or compressed configuration.
Figure 7B:
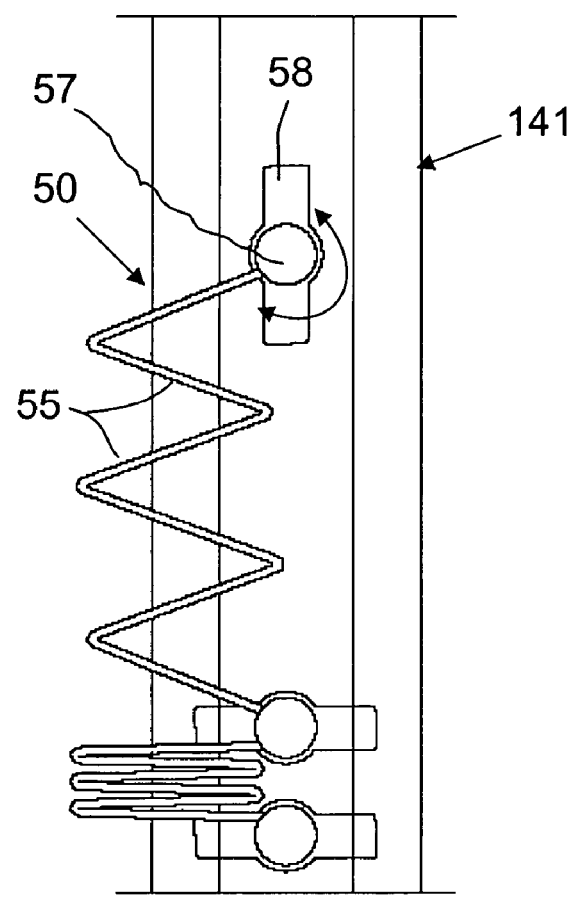

FIGS. 7A and 7B illustrate a further embodiment of the shielding panel provided in combination with the frame of the shielding member. In this case the shielding panel has a bellows or folding door type construction. Several adjacent strips 55 are hinged together at their facing edges by mechanical hinge elements or by flexible bridges of material. In the present embodiment, the flexible bridges are formed by the same material as the strips and folding lines are provided at the bridges consisting in a reduction of the thickness of the material or in partial cuts. The strips engage the upper and the lower guides with their shorter ends. In a compact arrangement, the shielding curtain or panel is folded on itself in such a way that the strips are oriented transversally to the sliding direction defined by the guides and the strips are laying one against the other with their larger surfaces. The shielding panel according to this embodiment can thus be shortened or lengthened between a minimum and a maximum length in the sliding direction. In addition, the shielding panel according to this embodiment can be displaced along the guides of the frame of the shielding member.

According to a further feature of the embodiment of FIGS. 7A and 7B, rotatable locking elements can be provided, which cooperate with the upper and lower guides, at certain distances along the overall length of the shielding panel in the extended position. The rotatable locking elements help in maintaining the shielding panel in a certain condition of elongation. The locking elements are provided at the ends of a rod 57 which is rotatably supported by some of the strips 55. Ends of the locking elements protrude inside the corresponding guide and over the corresponding edge of the strip or of the strips 55 by which the rod 57 is supported. The locking elements are secured at these protruding ends of the rotatable rod in a manner to rotate with the rod 57. The locking elements are formed by small levers 58 which can be rotated in a position parallel to the sliding direction and in a position transverse to the sliding direction of the panel. At these positions they protrude laterally outwardly from the two sides of the panel abutting against at least a wall of the guides to lock the panel or at least the strip or strips 55 by which the rod 57 is supported relatively to a sliding in the guide. As shown in FIGS. 7A and 7B, it is preferable for one rod 57 with the associated locking lever 58 to be supported at the free edge of the first strip 55 forming the panel and at least one further rod 57 with its locking levers to be supported at the free edge of the last strip 55. Further rods 57 with their associated locking levers are provided in intermediate positions of the shielding panel and preferably the rods are supported at the folding line or hinge between two adjacent strips 55 thus forming a hinge connecting the adjacent strips together.

Figure 8A:
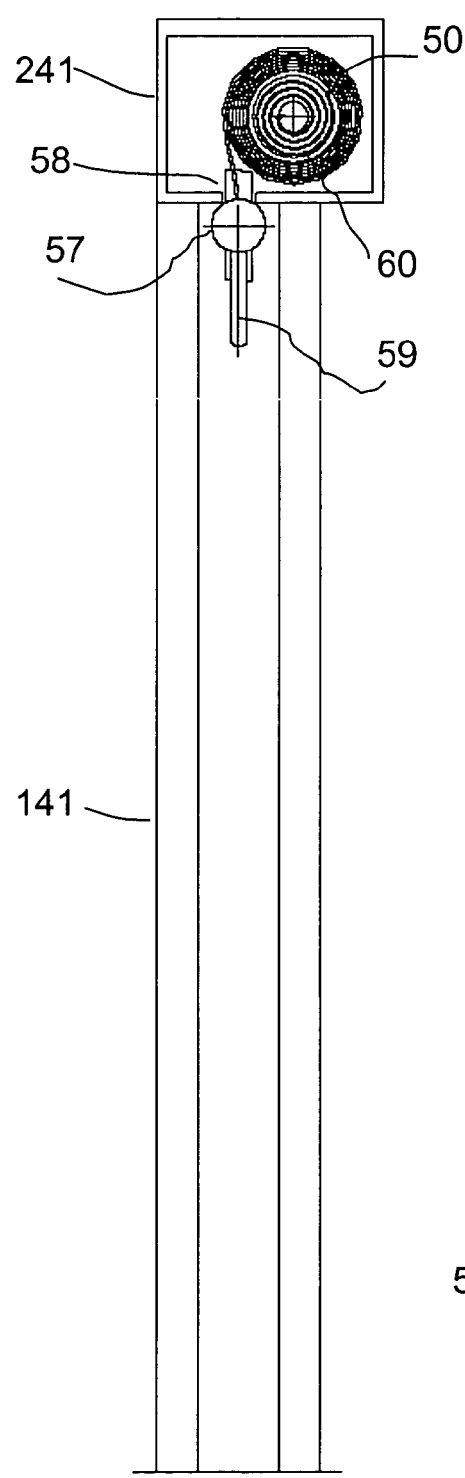
FIGS. 8A and 8B illustrate another embodiment in which the shielding panel or curtain is of the roller blind type.
Figure 8B:
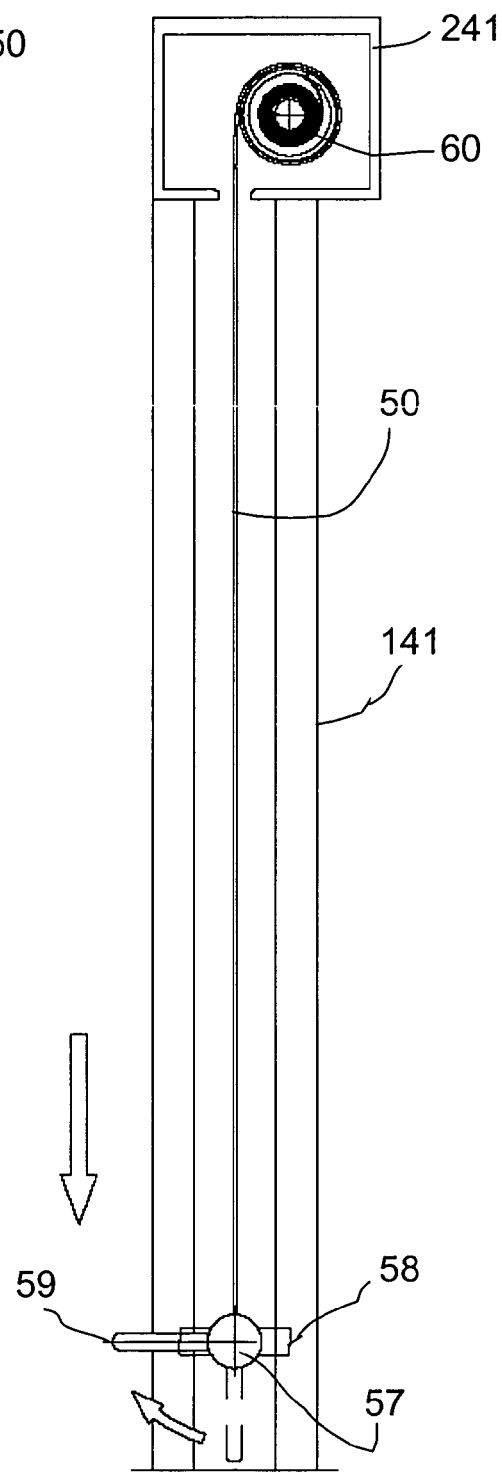

As disclosed in combination with the preceding embodiments, the shielding panel according to FIG. 8 is preferably made of electrically conductive material or is at least layered with a sheet or film of electrically conductive material. Furthermore, the electrical contact with the guides can be achieved by providing rotatable rods 57 and associated locking levers made of conductive material or having at least a layer of conductive material thus ensuring electrical contact between the shielding panel and the guides.

In an alternative construction of the shielding panel according to the present invention, a bellows or folding door type shielding panel is made of a shaped element of rubber or another elastic material. In its unstressed condition, the panel is in the compacted or closed condition corresponding to the condition of the minimum length in the sliding direction. The rods 57 can be embedded in the thickness of the rubber or elastic material by inserting the rods in the mold and injecting the rubber or elastic material. In the same way, a layer or a mesh of conductive elements such as electrically conductive wire mesh can be incorporated in the thickness of the rubber or of the elastic material.

Alternatively to the above described example, the shielding panel or the shielding curtain can be made of an elastic tissue or film which can be expanded in the direction of sliding in order to obtain differently sized shielding panels or curtains starting from a minimum length up to a maximum length defined by the elastic elongation capability of the specific elastic tissue or film.

FIGS. 8A and 8B, 9, 10, 11 and FIGS. 12A, 12B, 12C illustrate still another embodiment of the present invention in which the shielding member comprises a frame and at least one shielding curtain which is of the roll blind type.

In this embodiment, the transverse elements 241 connecting the ends of the upper and lower guides form a chamber, for example, if made tubular, the transverse elements house a roll 60 on which the shielding curtain 50 is wound. Either one or both of the transverse elements 241 may form a chamber for housing a roll 60. The edges of the shielding curtain 50 engaged in the upper and lower guides may have electrical contact elements or tracks similar to the shielding panels 50 of the previous examples. These electrical contact elements or tracks provide an electrical contact with electrical contact elements in the guides, for example as shown and described according to FIGS. 3A and 3B.

The shielding curtain may be made of a foil or tissue which may be electrically conductive or layered with an electrically conductive layer. The shielding curtain can be also made of extensible material. Furthermore, at the leading edge, with reference to the sliding direction of unwinding the shielding curtain, a locking mechanism can be provided for locking the curtain in a certain position within the guides. This is preferably if the roll is provided in combination with spring elements which automatically drive the roll in the winding direction. The locking mechanism can be made similar to the locking mechanism of the shielding panel according to the embodiment of FIGS. 7A and 7B. A rod 57 is rotatably mounted at the leading edge, for example, in a tubular hem made at the leading edge of the shielding curtain or in a tubular seat to which the leading edge of the shielding curtain is attached. The rod 57 carries at its ends (protruding inside the upper and lower guides) eccentric locking levers which can be rotated with the rod. The two locking levers 58 can assume a first position in which they do not interfere or come in contact with the walls of the upper and lower guides and a second position in which they come into contact with a wall of the upper and lower guides and generate a friction coupling to the guides which is sufficient to lock the shielding curtain in the unwind position against the force exerted by the automatic winding device associated to the roll 60.

Preferably, as shown in FIGS. 12A to 12E, the rod has, at one or more intermediate positions, one or more radial extensions 59 which serve as handles for rotating the rod 57 and the locking levers 58.

In the example of FIGS. 12A to 12E, the leading edge does not carry one rod but instead carries two half rods each one being associated to only one locking lever cooperating with the upper or lower guide. The two half rods are coaxial and each carries one radial lever for rotating the rods. FIGS. 12A to 12C illustrate a cross section according to a plane perpendicular to the upper and lower guides and below the position of the locking lever relatively to the guide as seen in the direction of the rod which corresponds to the position of the radial levers in the associate cross-section.

FIGS. 12C and 12E relate to a further variation which provides a panel according to FIGS. 1 to 7 in which the same mechanism of the locking levers is provided and in which the locking levers can be further used as a mechanism for engaging and disengaging the shielding panel from the guides, which is an alternative to the one illustrated in FIGS. 4A to 4C. In this case, the locking levers and the associated rods can be provided at both edges of the panel (which are transverse to the sliding direction) and even at several intermediate positions so that they can also be used for providing electrical contact between the shielding panel and the shielding frame. In this case, the rod and the locking levers are of electrically conductive material and the guides are provided at the surfaces coming into contact with the locking levers with electrically conductive tracks or a similar arrangement. For allowing sliding of the panel by maintaining the panel surely engaged in the guides, the friction between the levers and the walls of the guides can be at least partially reduced by providing an intermediate angular position in which the locking levers still cooperate with the walls of the guides but with a reduced contact surface.

Figure 13:
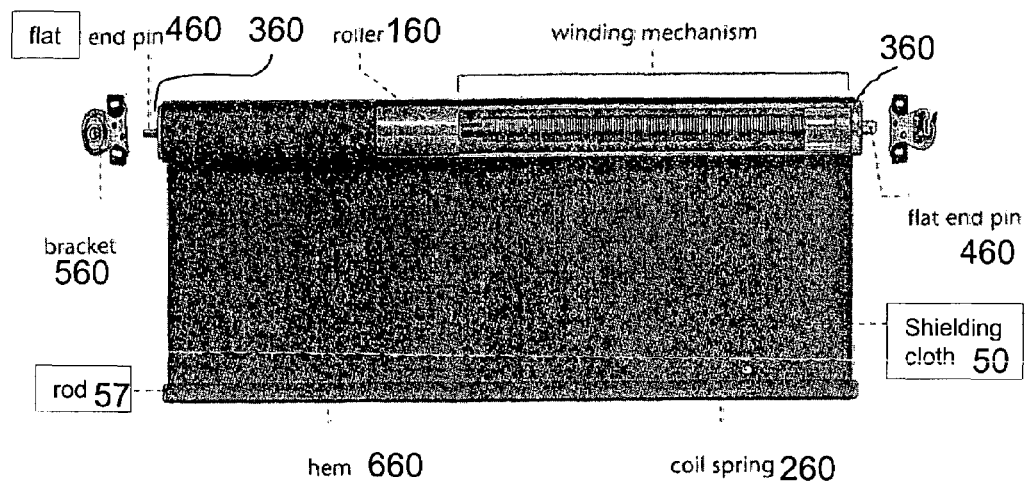
FIG. 13 illustrates a conventional roller blind arrangement which is applied to the roller blind type of shielding panel or curtain according to the present invention.

An example of the mechanism of the winding rod is illustrated in FIG. 13. A roller 160 is mounted on a roller mechanism comprising a spring 260 which is secured between the roller 160 and a stationary member on which the roller is rotatably mounted, such as for example the two end disks 360 which have an end pin such as a flat end pin 460. The flat end pins 460 engage a flat hole which can be provided in flat brackets 560 which are secured inside the tubular transverse element 241. The rod 50 is housed in a hem 660 of the leading edge of shielding cloth 50.

The roller illustrated in FIG. 13 is a typical roller blind mechanism which can be used without any considerable change in the present invention.

Obviously also other mechanisms can be used, for example, mechanisms of the known art having a self locking mechanism which stops the roller automatically and which can be released by further turning in the unwinding direction the shielding curtain or cloth before allowing the coil to rotate the roller in the winding direction. Such mechanisms are provided with ratchet gears which allow such functions.

FIG. 10 illustrates a side view of the shielding member 41 according to the present embodiment and in which the shielding curtain is a net or similar structure made of electrically conductive material.

FIG. 10 is a sectional view of FIG. 9 along a plane which is parallel to the guides and in which both transverse elements 241, connecting the ends of the upper and lower guides together, house a roller blind type shielding curtain. One of the shielding curtains is unwound for a length corresponding to the straight part of the guides and is also locked in this position, while the other is completely wound inside the roller. It has to be appreciated that the locking mechanism at the leading edge of the shielding curtains also has the function of limiting the winding since it abuts against a slit in the wall of the transverse elements 241 through which the shielding curtain passes outside of the transverse element 241. So in the completely wound up condition, the locking mechanism at the leading edge of the shielding curtains still remains outside the transverse element 241, having a width greater than the width of the slit.

FIG. 11 illustrates a variation in which, at least at the straight ends of the upper guide, the roller blind like shielding curtain is provided inside the straight part of the upper guide. In this case, the axis of the roller is parallel to the axis of the straight end of the upper guide. The rounded portion of the guide can be associated to sliding panels or curtains according to one or more of the preceding examples.

It is further worth noting that in this case the roll blind type shielding curtain can easily be provided with a non-rectilinear leading edge which can be shaped according to the morphology of the part to be examined which has to enter the apparatus, i.e. the imaging cavity of the magnetic structure 1. According to the previous example of FIG. 6A to 6C, the shielding curtain of the roller blind type can also be provided with shaped edges and/or with openings.

Figure 14:
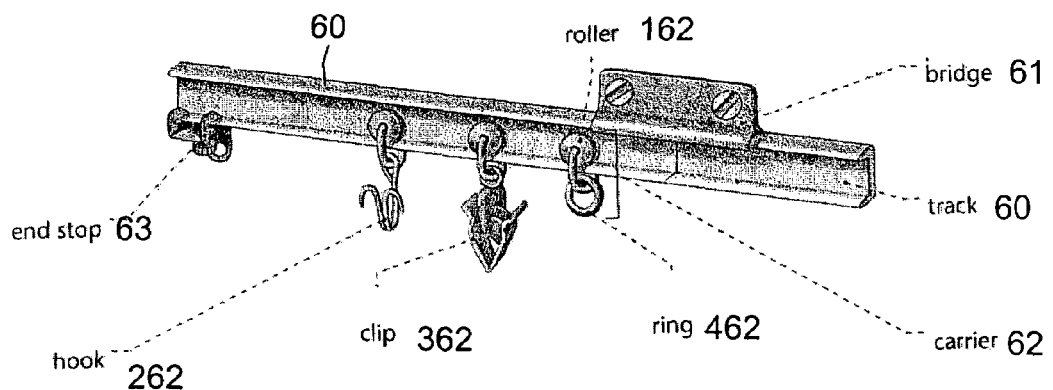
FIG. 14 illustrates a conventional curtain guide which is used for the shielding panel or for the shielding curtain according to the present invention.

According to a further variation of the preceding embodiments, the upper and lower guides may be constructed similarly to conventional curtain guides as, for example, the one illustrated in FIG. 14. In this case the electrical contact between the shielding curtain or panel 50 can be ensured by the guiding track 60 which is made or coated with electrically conductive material and which is secured to the upper and lower parts of the frame 141 of the shielding member 41. Also electrically conductive strips can be provided on the track. The track can be made of one piece or it can be formed by several segments which are connected mechanically and electrically by connection bridges 61. At the end of the tracks, end stops 63 can be provided. The shielding panels or shielding curtains 50 can be connected to the guiding tracks 60 by carriers 62 which are electrically conductive and which are provided with rolls 162 engaging the track and with hooks 262, clips 362 or rings 462 for securing the shielding panel or the shielding curtain 50 to the carrier 62. In this case, the elements of the frame corresponding to the upper and lower guide can be entirely of electrically non-conductive material.

Figure 15B:
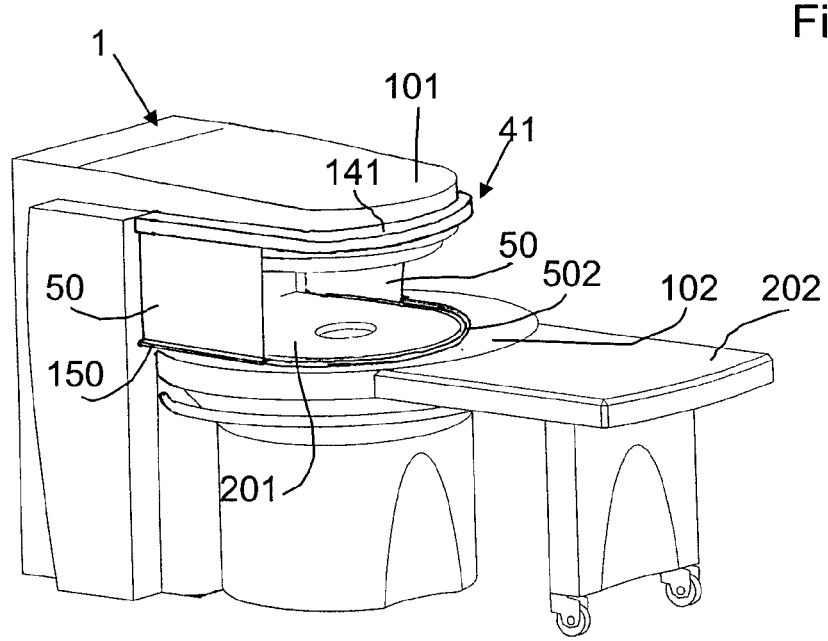

FIGS. 15A and 15B illustrate a further variation of the previous embodiments, in which the lower guide is not present.

In this case, the frame 141 of the shielding member comprises only the upper "U-shaped" guide which is hinged to the magnetic structure as in the previous example of FIG. 1. The shielding panels 50 or the shielding curtains are suspended from the upper guide and at their lower edges electrical contact elements 150 cooperate directly with electrical contact elements on the table part 102 of the table 2. The electrical contact elements 150 at the bottom edge of the shielding panel or shielding curtains 50 come into contact with an electrically conductive track 502 which surrounds the "U-shaped" opening 302 of the table 102 in which the lower side 201 of the magnetic structure penetrates when the table is brought against the magnetic structure 1.

FIG. 15B illustrates this condition. Furthermore, in FIG. 15A, an example of electrical contact elements provided between the table part 102 and the lower side of the magnetic structure 1 is shown. In this example, which is not limiting, the two contact surfaces of the "U-shaped" opening 302 of the table 102 and the "U-shaped" peripheral surface of the lower side 201 of the magnetic structure 1 respectively bear an electrically conductive track 402 which is coincident with a row of elastic contact elements 52 made according to the example of FIGS. 3A and 3B. Similar electrical contact elements are provided between the swingable "U-shaped" guide and the corresponding contact peripheral surface of the upper side 101 of the magnetic structure 1. In this case, the contact elements 52 are provided on the internal surface of the "U-shaped" upper guide while the electrically conductive track 402 is provided on the peripheral complementary surface of the upper part 101 of the magnetic structure.

Figure 16:
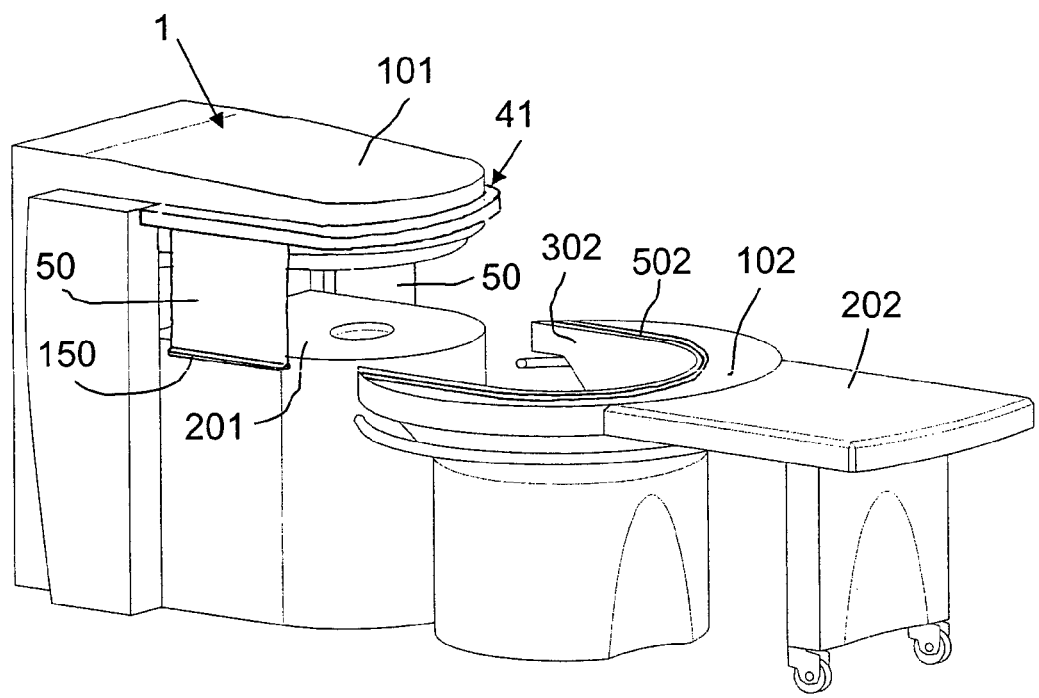
FIG. 16 illustrates a further variation of the embodiment of FIGS. 15A and 15B in which the upper guide is stationary and secured to the upper side of the magnetic structure and cannot be displaced relatively to it; and, FIG. 17 illustrates a further variation of the embodiments according to FIGS. 15A and 15B and 16 in which the shielding panel or the shielding curtain is of the roller blind kind.

FIG. 16 illustrates a variation in which the upper guide is not swingable but is stationary and secured to the peripheral surface of the upper side 101 of the magnetic structure.

Figure 17:
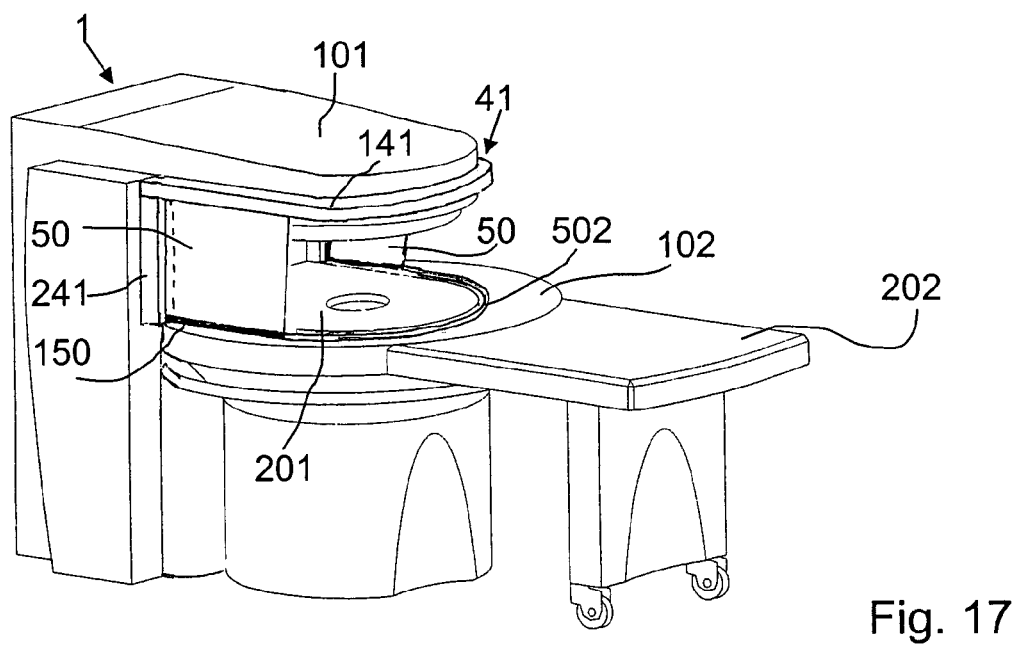

FIG. 17 is still another variation in which only the upper guide is provided in combination with a roller blind type shielding curtain or panel. In this case, both variations of FIGS. 15A and 15B and of FIG. 16 are possible.

Figure 18:
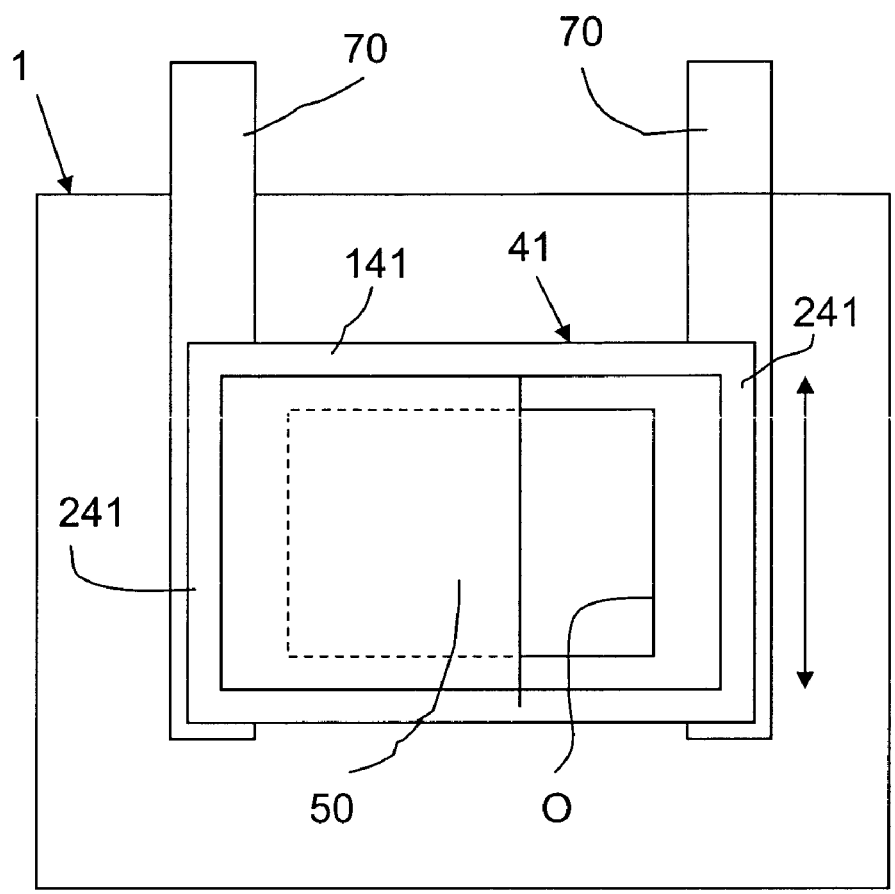

With reference now to FIG. 18, an annular magnetic structure is shown in a lateral view. In this case, the frame of the shielding member 141 is not secured in a swingable manner to the magnetic structure at its opening but is secured in a slidable manner within guides 70. In FIG. 18, the shield closes part of the open side of the magnetic structure 1, so that the opening "0" of the magnetic structure 1 is partially visible. Although this example does not illustrate a magnetic structure according to the previous examples, it is clear that a slidable shielding member can be provided also in combination with a magnetic structure as illustrated in FIG. 1 or 15A and 1b or 16 and 17. In this case, the transverse element 241 which connects the ends of the "U-shaped" guides or (with reference to FIGS. 15A and 15B) the ends of the upper guide, are engaged each one in one corresponding guide of two parallel vertical guides.

Further variations of the embodiments shown may comprise a shielding panel or curtain made of the Venetian blind kind. In this case, the frame 141 of the shielding member 41 has at least one upper element which corresponds to the Venetian blind classic upper rod. Alternatively, the Venetian blind-like shielding panel can be oriented vertically, and the ends of the strips forming the blind can be provided with one or more protrusions which engage either only one upper guide or one upper and one lower guide forming the frame.

A further variation relates to a magnetic structure 1 having at least one opening with a rounded or circular shape. In this case, the frame 141 of the shielding member 41 may be rectangular or square, while the one, three or four elements of the frame are aligned parallel or coincident with a tangential axis to the rounded or circular opening. The frame 141 inscribes or is a part of a square or rectangular element inscribing the opening of the magnetic structure 1.

A further variation relates to the shielding of a magnetic structure having more than one open side and where each opening of each open side is separated from an adjacent open side. This case applies, for example, in magnetic structures having two spaced apart substantially parallel poles which are held in their spaced apart position and connected by columns. In this case, a corresponding shielding member is associated to each open side. The shielding members can be of the identical type or each open side of the magnetic structure can be provided with a different shielding member construction chosen among the different types described above. The reason for this can be found in the different shapes and/or functions of the open sides relative to the kind of part of the body which has to access the imaging cavity of the magnetic structure and pass through a specific one of the open sides of the magnetic structure.

The present invention is not intended to be limited to the above description and illustrations, but may be greatly varied, especially with regard to the construction of the devices, without departing from the guiding principles disclosed above and claimed below.

What is claimed is:

1. A nuclear magnetic resonance imaging device, comprising:
    a magnetic structure defining an imaging cavity for housing at least part of a body of a patient, the magnetic structure providing a magnetic field for permeating at least part of the imaging cavity during imaging, the magnetic structure comprising an opening for the imaging cavity, said opening providing access to the imaging cavity from outside of the magnetic structure;
    shielding means for at least partially closing said opening of the imaging cavity, the shielding means comprising electrically conductive material and being electrically grounded, the shielding means being secured to the magnetic structure substantially adjacent said opening;
    guiding means for guiding the shielding means, the shielding means being movable along the guiding means from an inactive configuration in which the opening is substantially open to an active configuration in which the shielding means at least partially closes the opening;
    wherein the shielding means comprises an electrically conductive frame provided substantially adjacent the opening for the imaging cavity, the shielding means further comprising a shielding member, said guiding means further comprising a guide provided in said electrically conductive frame, said shielding member being slidably mounted in said guide, the guide being electrically conductive and the shielding member electrically conductive and electrically grounded.

2. A nuclear magnetic resonance imaging device according to claim 1, wherein the shielding member is made of a rigid material.

3. A nuclear magnetic resonance imaging device according to claim 1, wherein the shielding member has a length in the active configuration along the guide means which is shorter than the overall length of the opening along the guide means.

4. A nuclear magnetic resonance imaging device according to claim 1, wherein the shielding means comprises more than one shielding member, each shielding member having a different length in the direction of the guide means in the active configuration, further comprising coupling means for selectively coupling said shielding members together.

5. A nuclear magnetic resonance imaging device according to claim 1, wherein the shielding member comprises a curtain made of an electrically conductive tissue material or a foil material which is elastic.

6. A nuclear magnetic resonance imaging device according to claim 1, wherein the shielding member comprises a curtain defining a roller blind mounted with a roller axis which is perpendicular to the direction along said guide.

7. A nuclear magnetic resonance imaging device according to claim 1, wherein the shielding member comprises a curtain defining a roller blind having an axis of rotation which is parallel to the direction along at least part of said guide.

8. A nuclear magnetic resonance imaging device according to claim 1, wherein the shielding member comprises a curtain made of a flexible but inelastic tissue material or foil material, which tissue material or foil material is wound on a rotatable cylinder at one end of the guide of the frame of the shielding means to define a storage position, said rotatable cylinder being oriented with an axis of rotation oriented perpendicular to a direction along said guide, said cylinder being provided with resilient means for winding the shielding member on the cylinder, said resilient means being loaded by unwinding of said cylinder, and further comprising means for locking and unlocking the shielding member while said shielding member extends a predetermined extent along said guide.

9. A nuclear magnetic resonance imaging device according to claim 1, wherein the guide comprises an electrically conductive curtain rod which is electrically grounded, said shielding member being supported by said curtain rod by slidable carriers made of electrically conductive material which electrically contact said curtain rod and said shielding member.

10. A nuclear magnetic resonance imaging device according to claim 1 in which the shielding member is configured as a Venetian blind.

11. A nuclear magnetic resonance imaging machine according to claim 1 wherein the shielding member is configured as a sliding, folding door.

12. A nuclear magnetic resonance imaging device according to claim 1, wherein the shielding member is configured as a bellows.

13. A nuclear magnetic resonance imaging device according to claim 1, wherein the magnetic structure comprises more than one opening, said openings being separated one from the other by intermediate members of the magnetic structure, said shielding means comprising a shielding member for each of said openings.

14. A nuclear magnetic resonance imaging device according to claim 1, wherein said shielding means comprises at least two shielding members.

15. A nuclear magnetic resonance imaging device according to claim 14, wherein the shielding members are mounted in the frame of the shielding means.

16. A nuclear magnetic resonance imaging device according to claim 1, wherein the shielding means comprises a set of shielding members which can be mounted at the same time in the frame of the shielding member, said shielding members having different lengths in the direction of sliding in said guide.

17. A nuclear magnetic resonance imaging device according to claim 16, wherein at least one of said shielding members has a shaped opening.

18. A nuclear magnetic resonance imaging device according to claim 17, wherein said shaped opening is defined by an electrically conductive, compressible frame.

19. A nuclear magnetic resonance imaging device according to claim 1, wherein the shielding means comprises more than one shielding member which can be mounted at the same time in the frame of the shielding member, at least one of said shielding members having a side edge which is shaped so as to correspond to a shape of the part of the body of the patient to be examined.

20. A nuclear magnetic resonance imaging device according to claim 19, wherein said set of shielding members comprises a plurality of shielding members each having a differently shaped edge.

21. A nuclear magnetic resonance imaging device according to claim 1, in which the magnetic structure comprises at least two plane surfaces defining the imaging cavity, the shielding means comprising one or more shielding members, said electrically conductive frame being hinged to the magnetic structure about an axis at a first one of the two planes with said hinge axis being parallel to the said plane, said frame arranged to oscillate between a first position and a second position, said shielding means comprising a shielding curtain, said guide and said shielding curtain being electrically conductive and electrically grounded.

22. A nuclear magnetic resonance imaging device according to claim 21, wherein said guide means comprises two guides which are connected together at their ends by side elements, said guides being separated by a distance corresponding to the distance between the first plate and the second plate of the magnetic structure, said shielding curtain being slidably engaged in said sliding guides, the sliding guides and the shielding curtain being electrically conductive and in electrical contact one with the other and the sliding guides being electrically grounded through an electrically conductive hinge, said shielding curtain extending from one guide to the other guide, the lower guide further comprising electrically conductive contact elements which cooperate with electrically conductive contact elements on the lower plate of the magnetic structure so that when the shielding member is in the position for at least partially closing said opening of the magnetic structure, the electrically conductive contact elements at the lower guide come into electrical conductive contact with the electrically conductive contact elements on the second one of the two plates of the magnetic structure.

23. A nuclear magnetic resonance imaging device according to claim 22, wherein the side elements connecting together the upper and the lower guides of the frame of the shielding member are also electric conductive and in electrical conductive contact with the said guides and are electrically grounded through said hinge securing the frame of the shielding means to the magnetic structure, while the shielding member further comprises electrical contact elements at edges which are parallel with respect to said side elements of the frame of the shielding means.

24. A nuclear magnetic resonance imaging device according to claim 22, wherein the shielding curtain is configured as a roller blind, one of said side elements connecting together one end of the guides, thereby defining a case for housing a roller mechanism of the roller blind with said curtain being wound around a roller of said roller mechanism.

25. A nuclear magnetic resonance imaging device according to claim 21, wherein the upper guide of the guiding means is provided with electrically conductive contact elements which cooperate with electrically conductive contact elements on the upper plate of the two plates of the magnetic structure.

26. A nuclear magnetic resonance imaging device according to claim 21, wherein said shielding member comprises a rigid electrically conductive panel.

27. A nuclear magnetic resonance imaging device according to claim 21, wherein said shielding curtain is configured as a Venetian blind.

28. A nuclear magnetic resonance imaging device according to claim 21, wherein the shielding curtain is configured as a sliding folding door.

29. A nuclear magnetic resonance imaging device according to claim 21, wherein the shielding curtain is configured as a bellows.

30. A nuclear magnetic resonance imaging device, comprising:
   a magnetic structure defining an imaging cavity for housing at least part of a body of a patient, the magnetic structure providing a magnetic field for permeating at least part of the hinging cavity during hinging, the magnetic structure comprising an opening for the hinging cavity, said opening providing access to the imaging cavity from outside of the magneto structure;
   shielding means for at least partially closing said opening of the imaging cavity, the shielding means comprising electrically conductive material and being electrically grounded, the shielding means being secured to the magnetic structure substantially adjacent said opening;
   guiding means for guiding the shielding means, the shielding means being movable along the guiding means from an inactive configuration in which the opening is substantially open to an active configuration in which the shielding means at least partially closes the opening;
   wherein the shielding mans comprises an electrically conductive frame provided substantially adjacent the opening for the imaging cavity, the shielding means further comprising a shielding member, wherein the opening of the magnetic structure is defined by an upper edge, a lower edge and side edges connecting the lower and upper edges, the frame of the shielding means defining an opening having edges which are substantially parallel to the edges of the opening of the magnetic structure, said guiding means further comprising an upper sliding guide from which the shielding member hangs down, said upper sliding guide being provided in said electrically conductive frame, said shielding member being slidably mounted in said upper sliding guide, the upper sliding guide being electrically conductive and the shielding member being electrically conductive and electrically grounded, the shielding member being provided with electrical contacts at a lower edge opposite to the upper sliding guide.

31. A nuclear magnetic resonance imaging device according to claim 30, wherein said upper sliding guide is substantially at the upper edge of the opening of the magnetic structure and the lower guide is substantially at the lower edge of the opening of the magnetic structure, the upper and lower guides each having ends which are connected together by side elements of the frame of the shielding means, the shielding member having upper and lower edges slidably engaged with the upper and lower guides.

32. A nuclear magnetic resonance imaging device according to claim 31, wherein at least one of the upper and lower guides is electrically conductive and electrically grounded through the frame of the shielding means to the magnetic structure, said shielding member being electrically conductive and in electrical contact with electrically conductive sliding elements at the edges of the shielding member engaging the upper and lower guides.

33. A nuclear magnetic resonance imaging device according to claim 31, wherein at least one of the side elements connecting the upper and lower guides of the frame of the shielding means is electrically conductive and in electrical contact with an electrically conductive contact member at the corresponding edge of the shielding member.

34. A nuclear magnetic resonance imaging device comprising:
   a U-shaped magnetic structure including two opposite poles defining an imaging cavity, said two opposite poles generating a magnetic field, said two opposite poles being supported in a spaced apart relationship by a ferromagnetic yoke having at least two opposite plates to which the poles are secured and a side member connecting the two opposite plates together and maintaining the two plates apart by a predetermined distance, whereby the side member defines the imaging cavity on at least one side, the pores and the pole supporting plates being supported in a cantilevered manner by the side member and the imaging cavity being open on other sides which are perpendicular to the plane of said poles, and
   shielding means for at least partially closing said open sides of said imaging cavity, said shielding means comprising an upper guide and a lower guide extending continuously along a perimeter of the opening, the upper guide and the lower guide being connected together by side elements at the two opposite ends of the guides, the guides and the side elements forming a frame of said shielding means, said side elements being provided substantially adjacent corresponding edges of the side member of the yoke, said frame of the shielding means being hinged to the magnetic structure at the ends of the upper guide, said frame being movable about an axis which is substantially parallel to a plane of said side member and to a plane of said upper plate of the yoke, at least one sliding shielding members being provided between the upper guide and the lower guide.

35. A nuclear magnetic resonance imaging device according to claim 34, wherein the opposite poles of the magnetic structure are substantially only connected to each other over only a small portion of the perimeter of the poles, a plurality of shielding members being provided which are sufficient to substantially cover an entire open portion of said perimeter of the poles of the yoke.

36. A nuclear magnetic resonance imaging device according to claim 34, further comprising flexible shielding members, such as cushions, curtains, and sleeves, which are electrically conductive and which contact the shielding means both mechanically and electrically.

37. A nuclear magnetic resonance imaging device according to claim 34, wherein the shielding member comprises electrically conductive material or comprises at least a layer of electric conductive material, said shielding member further comprising electrical contact elements which are in an electrically conductive relationship with guides, said guides being electrically grounded.

* * * * *